United States Patent
Nevin

(10) Patent No.: US 8,231,435 B2
(45) Date of Patent: Jul. 31, 2012

(54) SANITIZING DENTAL MODEL TRIMMER

(76) Inventor: Donald Nevin, Woodbury, NY (US)

(*) Notice: Subject to any disclaimer, the term of this patent is extended or adjusted under 35 U.S.C. 154(b) by 580 days.

(21) Appl. No.: 12/460,147

(22) Filed: Jul. 14, 2009

(65) Prior Publication Data

US 2010/0203464 A1  Aug. 12, 2010

Related U.S. Application Data

(60) Provisional application No. 61/132,105, filed on Jun. 16, 2008, provisional application No. 61/207,230, filed on Feb. 10, 2009.

(51) Int. Cl.
*B24B 7/00* (2006.01)
*B24B 55/04* (2006.01)

(52) U.S. Cl. .............. 451/67; 433/29; 433/51; 451/359; 451/450; 451/451

(58) Field of Classification Search ............... 144/251.1; 433/29, 51; 451/65, 67, 259, 450, 451, 358, 451/359
See application file for complete search history.

(56) References Cited

U.S. PATENT DOCUMENTS

| 4,558,686 A | * | 12/1985 | Ono | 125/13.01 |
| 4,698,206 A | * | 10/1987 | Nevin | 422/24 |
| 2003/0150905 A1 | * | 8/2003 | Mazzilli | 232/17 |

OTHER PUBLICATIONS

Mori, M. et al, Short Communication—Development of a new water sterilization device with a 365nm UV-LED pub. Nov. 3, 2007.
Buffalo Dental Manufacturing Co., Inc. Wet Model Trimmers,Catalogue Page, USA.
Specifications for Nichia Chip Type UV LED—Model NCSU033A(T) Nichia Corporation No. STSE-CC6130A—Cat. No. 061218.

* cited by examiner

*Primary Examiner* — Timothy V Eley
(74) *Attorney, Agent, or Firm* — Robert L. Epstein; Epstein Drangel LLP

(57) ABSTRACT

The dental model trimmer includes a wheel having an abrasive surface, a motor for rotating the wheel, and ultraviolet light source powerful enough to inactivate bacteria. The components are located in an enclosure that has an opening to permit access to the abrasive surface of the wheel. The light source is mounted within the enclosure to illuminate a section of the abrasive surface of the wheel that is spaced from the access opening. The enclosure includes wall means interposed between the light source and the access opening for preventing direct light emitted from the UV light source from exiting the access opening. The enclosure is provided with an interlock switch that will automatically turn off the light source when the enclosure is opened. The same switch can be used to deactivate the motor and a source of water provided to the abrasive surface, if desired.

16 Claims, 4 Drawing Sheets

SANITIZING DENTAL MODEL TRIMMER

CROSS-REFERENCE TO RELATED APPLICATIONS

Priority is claimed on Provisional Patent Application No. 61/132,105 filed Jun. 16, 2008 and Provisional Patent Application No. 61/207,230 filed Feb. 10, 2009.

STATEMENT REGARDING FEDERALLY SPONSORED RESEARCH OR DEVELOPMENT

Not Applicable

REFERENCE TO A "SEQUENCE LISTING", A TABLE, OR A COMPUTER PROGRAM LISTING APPENDIX SUBMITTED ON COMPACT DISC

Not Applicable

BACKGROUND OF THE INVENTION

1. Field of the Invention

The present invention relates to dental model trimmers and more particularly to a dental model trimmer with an internal sanitizing ultraviolet light source 2. Description of Prior Art Including Information Disclosed Under 37 CFR 1.97 and 1.98

A dental model trimmer is an abrasive grinder used to finish and trim models of teeth and oral structures. The trimmer has a rotating wheel with an abrasive surface against which the piece being formed is pressed to shape the piece. The abrasive surface may be formed of carborundum, diamond, silicon carbide or other abrasive material. The wheel is rotated at high speed, for example 3600 RPM, by a high torque electric motor.

The wheel is situated within an enclosure which has an access opening. With the wheel rotating, the operator inserts the piece being worked through the access opening in the enclosure and presses it against the abrasive surface of the rotating wheel to work the piece. During this process, water is sprayed onto the wheel from a nozzle located within the enclosure to wash away particles as they are removed from the piece and to cool the wheel surface.

Due to the source of the original materials of the models being trimmed, the pieces being worked may contain bacteria and other microorganisms. Those organisms can build up on the abrasive surface of the wheel, even though the wheel is being continuously flushed by water while in operation.

It is known that ultraviolet light from a light source, such as a high-powered LED emitting light in a particular UV wavelength range, is effective in a wet environment to inactivate bacteria. Thus, such a light source can be used as a sterilization device. However, since a LED with sufficient power to sterilize radiates intense UV light during operation, precautions must be taken to prevent the operator from looking directly at the UV light with the unaided eyes or through an optical system.

The present invention provides a structure in which a high intensity UV light source can be used in a dental model trimmer to disinfect the abrasive surface of the grinding wheel without injuring the eyes of the operator.

It is, therefore, a prime object of the present invention to provide a dental model trimmer capable of disinfecting the abrasive surface of the grinding wheel.

It is another object of the present invention to provide a sanitizing dental model trimmer that is safe for the operator to use.

It is another object of the present invention to provide a sanitizing dental model trimmer which utilizes a high-powered ultraviolet light emitting LED to sanitize the grinding wheel.

It is another object of the present invention to provide a sanitizing dental model trimmer which includes an enclosure within which the UV LED is mounted.

It is another object of the present invention to provide a sanitizing dental model trimmer in which the enclosure has an access opening and means for preventing light from the UV LED from exiting the access opening.

It is another object of the present invention to provide a sanitizing dental model trimmer in which the light preventing means takes the form of a wall extending from the interior surface of the enclosure.

It is another object of the present invention to provide a sanitizing dental model trimmer in which the light preventing means also includes the wall surrounds at least the portion of the edge of the access opening facing the UV LED.

It is another object of the present invention to provide a sanitizing dental model trimmer in which the enclosure is formed of two separable sections and includes an interlock that automatically deenergizes the UV LED when the sections are separated to access the interior of the enclosure.

BRIEF SUMMARY OF THE INVENTION

In general, the above stated objects are attained by the present invention which relates to a sanitizing dental model trimmer that includes a wheel having an abrasive surface and means for rotating the wheel. The trimmer has ultraviolet light source and means for energizing the light source. An enclosure for the wheel is provided having an opening to permit access to the abrasive surface of the wheel. Means are provided for mounting the light source within the enclosure at a location spaced from the access opening. Means interposed between the light source and the access opening are provided for preventing direct light from the light source from exiting the access opening.

The enclosure has an interior surface to which the light source is mounted. The light source is mounted at a location on the interior surface spaced from the access opening.

The light preventing means includes a wall situated between the light source and the access opening. The wall extends from the interior surface of the enclosure in a direction substantially perpendicular to the interior surface.

The light preventing means includes a wall which extends from the interior surface of the enclosure and around at least a portion of the edge of access opening facing the light source means.

The enclosure substantially encloses the abrasive surface of the wheel, other than the section thereof aligned with the access opening.

The enclosure is formed of first and second sections. Means are provided for joining the first and second sections. Means are also provided for deactivating the light source when the first and second sections of the enclosure are separated.

The light source emits a UV light of sufficient intensity to inactivate bacteria on the abrasive surface of the wheel. Preferably, the light source takes the form of a light emitting diode. The light source preferably emits ultraviolet light in a wavelength range between 360 nm and 370 nm. The light source most preferably emits ultraviolet light at a wavelength of approximately 365 nm.

BRIEF DESCRIPTION OF THE SEVERAL VIEWS OF DRAWINGS

To these and to such other objects that may hereinafter appears, the present invention relates to a sanitizing dental model trimmer as described in detail in the following specification and recited in the annexed claims, taken together with the accompanying drawings, in which like numerals refer to like parts and in which:

DETAILED DESCRIPTION OF THE INVENTION

Figure 1:
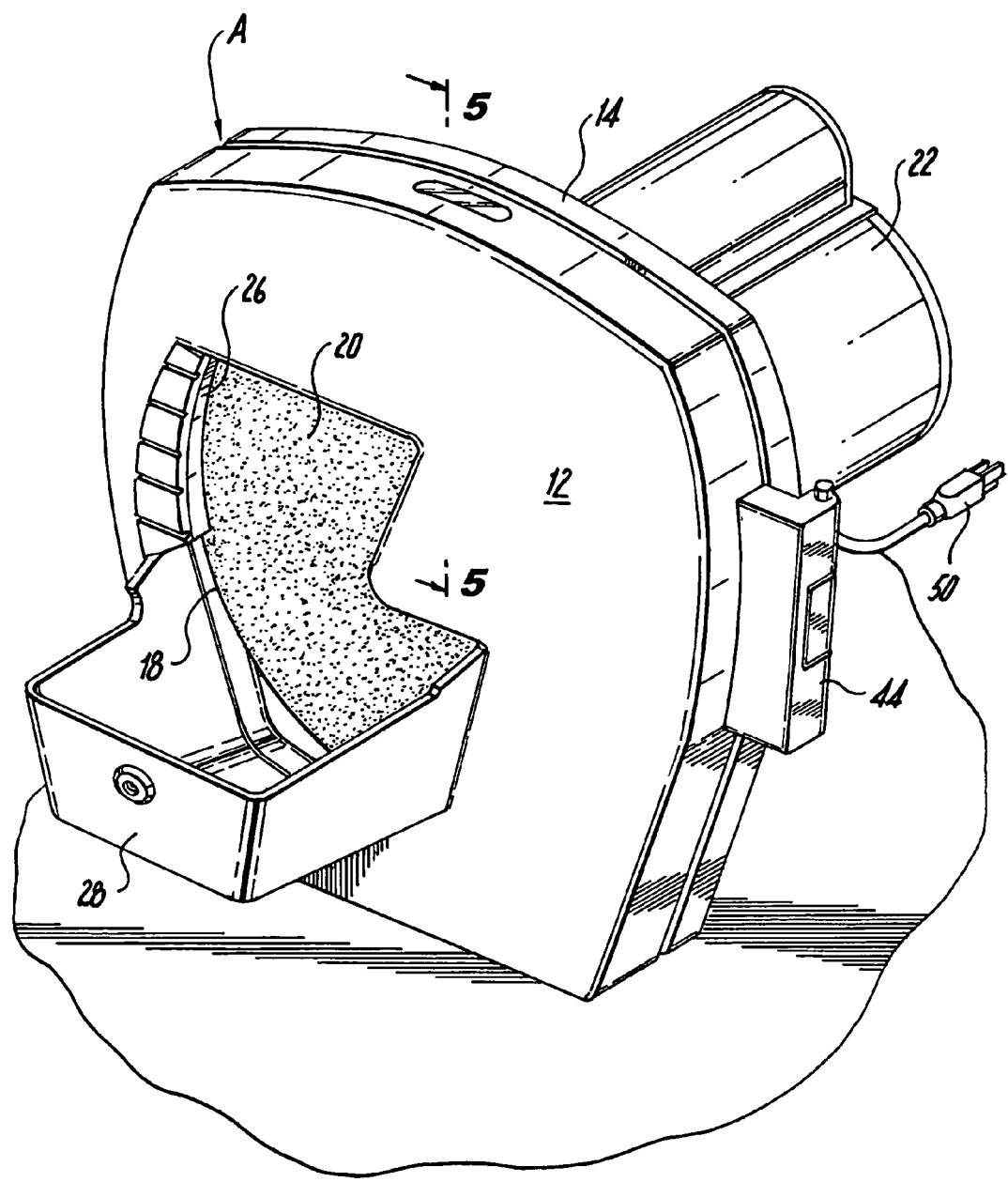
FIG. 1 is a perspective view of the exterior of the dental model trimmer of the present invention as seen from the front.
Figure 2:
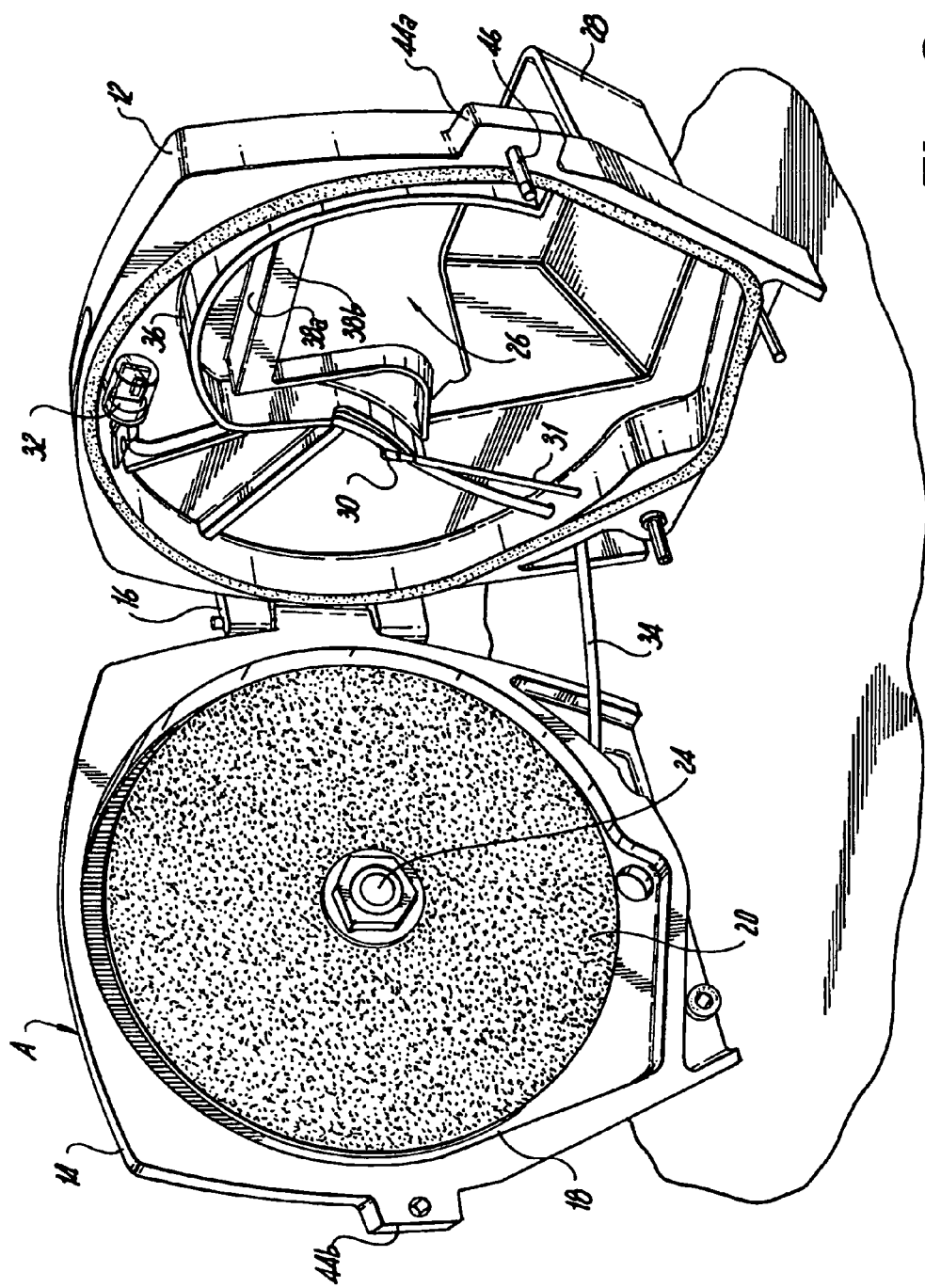
FIG. 2 is a perspective view of the interior of the dental model trimmer of FIG. 1, showing the housing sections open.

The sanitizing dental model trimmer of the present invention, generally designated A, consists of a housing 10 including a front section 12 and a rear section 14. Housing sections 12 and 14 are connected together by a hinge 16 and can be moved between a closed position (FIG. 1) and an open position (FIG. 2). During operation of the trimmer, the housing sections are always closed, as seen in FIG. 1. However, when not in operation, the housing sections can be opened for access to the interior of the trimmer, as seen in FIG. 2, for component replacement, cleaning or repair.

Housing 10 encloses a grinding wheel 18 having an abrasive surface 20. The wheel is typically 10 or 12 inches in diameter. Surface 20 may be formed of diamond, Carborundum or other suitable abrasive material. Instead of the abrasive surface being part of the wheel itself, a disposable silicon carbide abrasive disk may be attached to an aluminum backing to form the grinding wheel.

A rearward extending section 22 of housing portion 14 holds an electric motor (not shown) which drives an output shaft 24 keyed to wheel 18 to rotate the wheel when the motor is energized, as is conventional. The motor is typically a ⅓ or ½ horsepower, 120 V or 220V AC 60 Hz motor.

The trimmer is used to finish and trim models of teeth and oral structures. With wheel 18 rotating, the workpiece is held against abrasive surface 20 of wheel 18 through window 26 in front section 12 of the housing. A tray 28 extending outwardly from the exterior surface of housing section 12 is provided to support a table (not shown) upon which the workpiece is placed as it is being formed during the grinding process.

As the grinding process is taking place, it is advantageous to keep abrasive surface 20 wet by spraying water onto the portion of the grinding surface being used to grind the workpiece. A nozzle 30 (see FIGS. 5 and 6) is provided for that purpose. Nozzle 30 is connected to a pressurized water supply through a water supply tube 31. A water control solenoid valve (not shown) situated in the water supply tube may be used to control the water supply to the nozzle. A water exhaust hose (also not shown) may be used to remove water from the housing after it has been sprayed from the nozzle.

It is known that irradiation of a surface with light from certain types of sources, such as from a UV-LED, will effectively sterilize a surface by inactivating certain bacteria in a wet environment. Such a light source preferably emits ultraviolet light in a wavelength range between 360 nm and 370 nm. The light source most preferably emits ultraviolet light at a wavelength of approximately 365 nm. The present invention uses such a UV LED light source, for example, one or more Model NCSU033A(T) chip type UV LEDs from Nichia Corporation, for this purpose.

Accordingly, the trimmer of the present invention utilizes an ultraviolet light source in order to inactivate bacteria in a wet environment on the abrasive surface of the grinding wheel. The light source is connected to a means for energizing the light source such as a 120 V AC outlet (not shown) by a conduit 34. The light source may be one or more LEDs 32 mounted within housing 10, as is seen in FIGS. 2, 3, 5 and 6, in which case the energizing means will be a source of electricity connected to the LED by wires 34. Alternatively, the light source may be an optical fiber bundle 34 terminating within the housing at location 32, in which case the LED itself will be located at a remote location, at the other end of the bundle. In either case, a lens, light guide or other light focusing or directing means may be employed.

As noted above, the ultraviolet light from such a powerful light source is damaging to the naked eye. Since the operation of the trimmer requires the operator to closely observe the workpiece through the access window as it is being trimmed to the desired shape and size, the use of this type of light source to inactivate bacteria on the grinding wheel would normally not be possible. However, in the present invention the light source is mounted and the housing is structured in a way that avoids any direct light from the light source from exiting the access window. The light therefore cannot enter the eyes of the operator and hence cannot cause any damage to the eyes of the operator.

The light source is mounted within the housing so as to illuminate a section of the abrasive surface 20 of wheel 18 spaced from the access window, that is, a section of the abrasive surface remote from that which is being used to trim the workpiece as the wheel rotates. Further, the housing includes means interposed between the light source and the access window for preventing direct light from the light source from exiting the access window and damaging the eyes of the operator during the trimming process. Accordingly, the light source is mounted at a location within the housing, and the housing is configured in such a manner as to protect the eyes of the operator from damage as the trimmer is used.

As seen in FIG. 2, light source 34 is mounted to the interior surface of front section 12 of housing A at point across from the top of the abrasive surface, spaced from access window 26. Thus, when the light source is energized it will illuminate a section of the rotating wheel remote from the access window.

Figure 5:
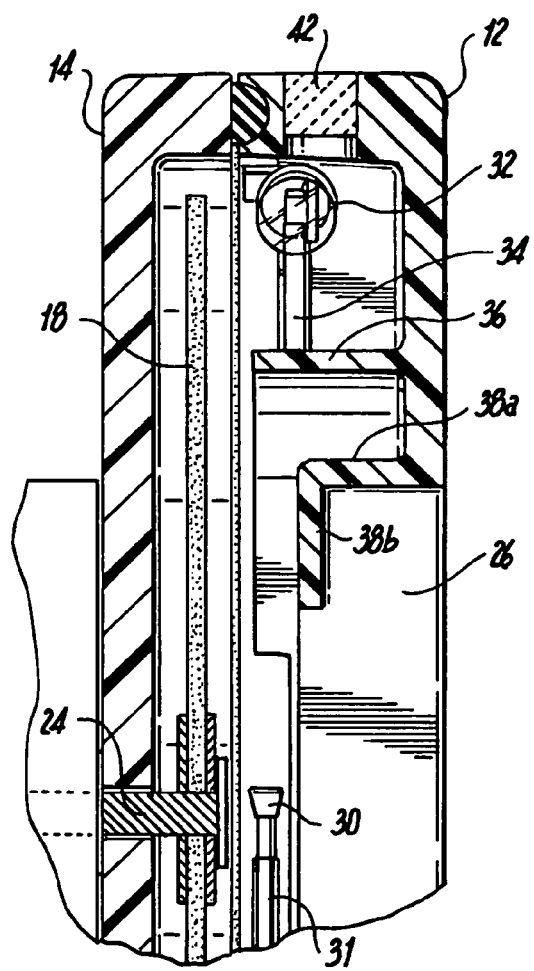
FIG. 5 is a cross-sectional view taken along line 5-5 of FIG. 1 showing the trimmer components turned off.
Figure 6:
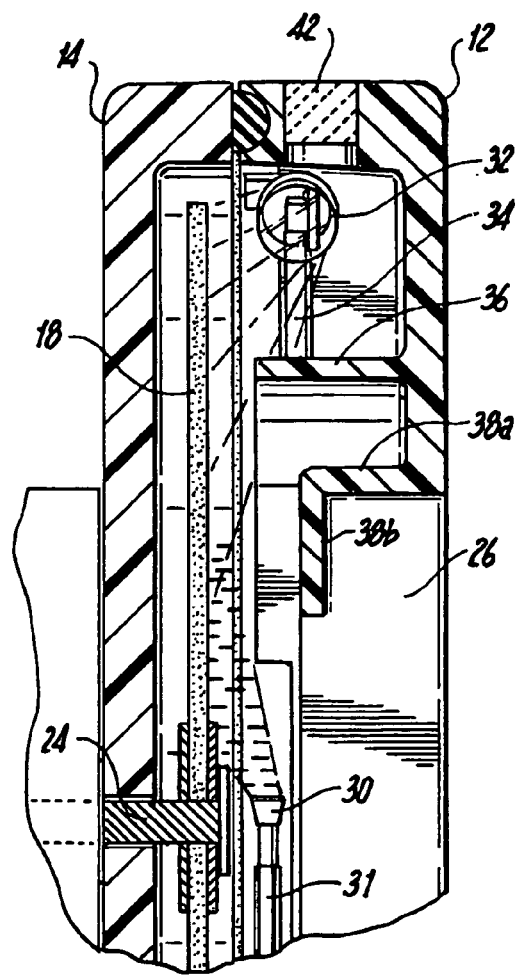
FIG. 6 is a view similar to FIG. 5 but showing the trimmer components operative.

Further, as best seen in FIGS. 5 and 6, the interior surface of housing section 12 has a wall 36 which extends in a perpendicular direction from the interior surface of housing section 12. Wall 36 is interposed between light source 32 and access window 26. Wall 36 acts to prevent any direct light emitted from light source 32 from exiting access opening 26.

Further, housing section 12 also has second wall 38, which partially defines the edge of access window 26 facing the light source. Wall 38 has a section 38a situated parallel to and spaced from wall 36. It also has a section 38b which extends perpendicular to section 38a and is parallel to but spaced from wheel 18. Wall 38 provides an extra barrier for preventing direct light from light source 32 from exiting access window 26.

Figure 3:
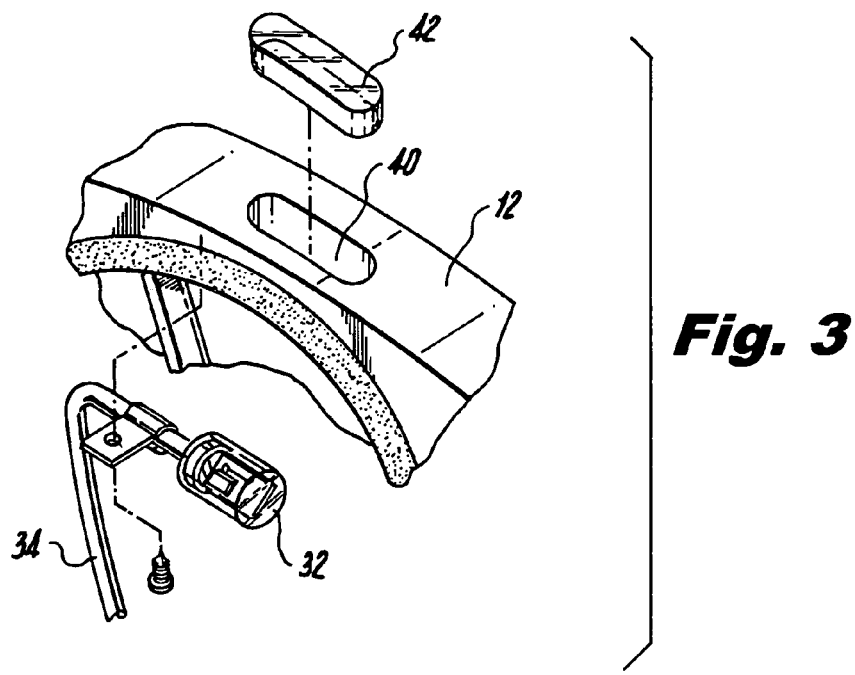
FIG. 3 is an exploded view of a portion of the trimmer housing showing the LED and viewing lens.

As seen in FIG. 3, the top edge of section 12 of the housing has an opening 40 aligned with light source 32. A light attenuating lens 42 is situated within opening 40. Lens 42 acts as a filter preventing harmful light from light source 32 from passing through it. However, enough harmless light from the light source can pass through lens 42 to permit the operator to observe the attenuated light from the light source source and know that same is functioning.

Figure 4:
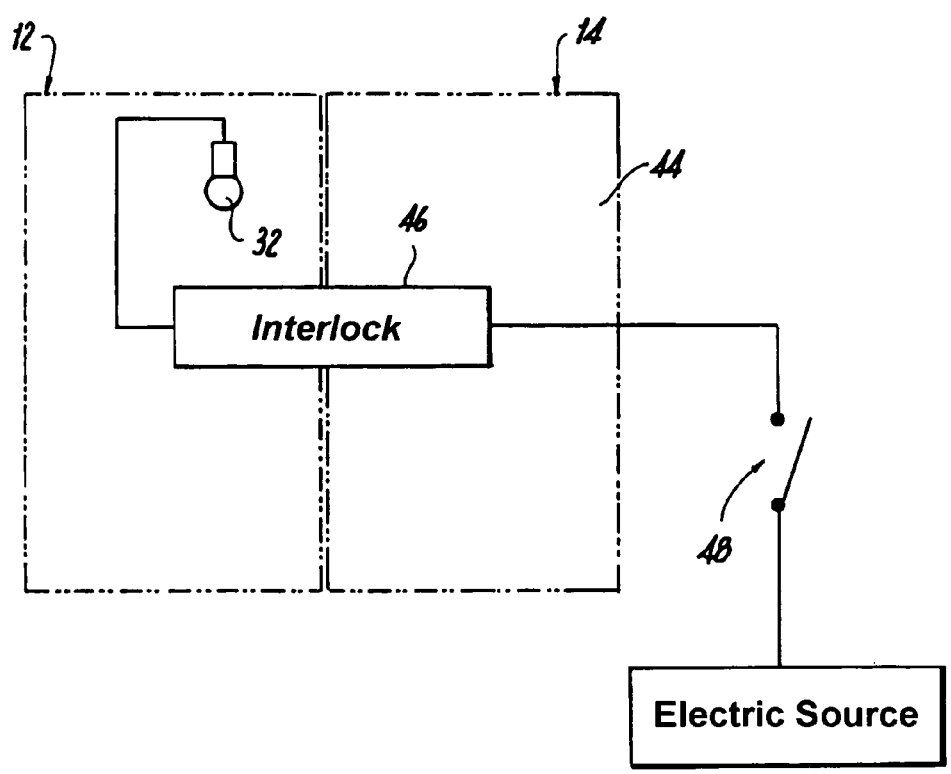
FIG. 4 is a schematic drawing of the light source interlock switch.

Referring now to FIGS. 2 and 4, the housing sections 12 and 14 are provided with interlock switch sections 44a and 44b that protrude outwardly from the edge of the housing at a point opposite to hinge 16. Interlock switch section 44a includes a depressible actuator 46 spring-loaded toward the extended position, as see in FIG. 2. Actuator 46 aligns with section 44b and is depressed when the housing sections 12 and 14 are closed. The depression of actuator 46 closes the contacts of a switch 48 situated within section 44a. The depression of the actuator causes switch 46 is connect light source 32 to an electric source, such as an electrical outlet (not shown) into which plug 50 is received.

Preferably, interlock switch 48 also controls the energization of the motor that rotates wheel 18 as well as the solenoid valve which may be provided to control the water supply to nozzle 30. Thus, opening of the housing will automatically simultaneously turn off all power to the motor and to the light source, as well as turn off the water supply.

It will now be appreciated that the present invention relates to a dental model trimmer including a wheel having an abrasive surface, a motor for rotating the wheel, and ultraviolet light source powerful enough to inactivate bacteria. The components are located in an enclosure that has an opening to permit access to the abrasive surface of the wheel. The light source is mounted within the enclosure to illuminate a section of the abrasive surface of the wheel that is spaced from the access opening. The enclosure includes wall means interposed between the light source and the access opening for preventing direct light emitted from the UV light source from exiting the access opening.

The enclosure is provided with an interlock switch that will automatically turn off the light source when the enclosure is opened. The same switch can be used to deactivate the motor and a source of water provided to the abrasive surface, if desired.

While only a single preferred embodiment of the present invention has been disclosed for purposes of illustration, it is obvious that many modifications and variations could be made thereto. It is intended to cover all of those modifications and variations which fall within the scope of the present invention, as defined by the following claims.

I claim:

1. A dental model trimmer comprising an enclosure, a wheel situated within said enclosure having an abrasive surface, means for rotating said wheel, an ultraviolet light source, means for energizing said light source, said enclosure comprising an access opening to permit access to said abrasive surface of said wheel, means for mounting said light source within said enclosure in alignment with a section of said abrasive surface spaced from said access opening, and means interposed between said light source and said access opening for preventing direct light emitted from said light source from exiting said access opening.

2. The trimmer of claim 1 wherein said enclosure comprises an interior surface to which said light source is mounted.

3. The trimmer of claim 1 wherein said light source is mounted at a location spaced from said abrasive surface.

4. The trimmer of claim 1 wherein said light preventing means comprises a wall situated between said light source and said access opening.

5. The trimmer of claim 1 wherein said light preventing means forms part of said enclosure.

6. The trimmer of claim 1 wherein said enclosure has an interior surface and wherein said light preventing means extends from the interior surface of said enclosure.

7. The trimmer of claim 1 wherein said access opening comprises an edge, and wherein said light preventing means extends around at least a portion of said edge of said access opening facing said light source.

8. The trimmer of claim 1 wherein said enclosure has an interior surface, and wherein said light preventing means comprises a wall which extends from said interior surface in a direction substantially perpendicular to said interior surface.

9. The trimmer of claim 1 wherein said enclosure substantially encloses said abrasive surface of said wheel other than the section of said abrasive surface aligned with said access opening.

10. The trimmer of claim 1 wherein said enclosure comprises first and second housing sections movable between closed and open positions and means for deactivating said light source when said first and second housing sections are in said open position.

11. The trimmer of claim 1 wherein said light source emits a UV light of sufficient intensity to inactivate bacteria on said abrasive surface of said wheel.

12. The trimmer of claim 1 wherein said light source comprises a light emitting diode.

13. The trimmer of claim 1 wherein said light source emits ultraviolet light in a wavelength range between 360 nm and 370 nm.

14. The trimmer of claim 1 wherein said light source emits ultraviolet light at a wavelength of approximately 365 nm.

15. The trimmer of claim 1 further comprising means for spraying water on said abrasive surface.

16. The trimmer of claim 1 further comprising an attenuating lens in said enclosure to permit said light source to be observed without harm.

* * * * *